(12) United States Patent
Snyder et al.

(10) Patent No.: US 6,553,257 B2
(45) Date of Patent: Apr. 22, 2003

(54) INTERACTIVE METHOD OF PERFORMING CARDIPULMONARY RESUSCITATION WITH MINIMAL DELAY TO DEFIBRILLATION SHOCKS

(75) Inventors: David Snyder, Bainbridge Island, WA (US); Carlton Morgan, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/804,398

(22) Filed: Mar. 13, 2001

(65) Prior Publication Data

US 2002/0133197 A1 Sep. 19, 2002

(51) Int. Cl.[7] .................................................. A61N 1/39
(52) U.S. Cl. ......................................................... 607/5
(58) Field of Search ................................. 607/5, 6, 7, 8

(56) References Cited

U.S. PATENT DOCUMENTS

| 5,607,454 A | 3/1997 | Cameron et al. |
| 6,021,349 A | * 2/2000 | Arand et al. |
| 6,334,070 B1 | * 12/2001 | Nova et al. |
| 6,370,428 B1 | * 4/2002 | Snyder et al. |

FOREIGN PATENT DOCUMENTS

| WO | WO94/27674 | 12/1994 |

* cited by examiner

*Primary Examiner*—Scott M. Getzow

(57) ABSTRACT

A method for reducing delay between termination of cardiopulmonary resuscitation and administration of a defibrillating shock. An electrocardiogram signal of the patient is monitored during administration of cardiopulmonary resuscitation to a patient. The electrocardiogram signal is analyzed to determine whether a shockable rhythm exists. It is indicated that a shockable rhythm exists and/or that a defibrillating shock will be administered. Cardiopulmonary resuscitation is stopped. The defibrillating shock is administered within 10 seconds of the cessation of cardiopulmonary resuscitation.

30 Claims, 2 Drawing Sheets

INTERACTIVE METHOD OF PERFORMING CARDIPULMONARY RESUSCITATION WITH MINIMAL DELAY TO DEFIBRILLATION SHOCKS

BACKGROUND OF THE INVENTION

1. Field of the Invention

The present invention relates to external defibrillators. In particular, the present invention relates to a method and device for minimizing delay between the cessation of cardiopulmonary resuscitation and the delivering of a defibrillating shock to a patient.

2. Description of Prior Art

Sudden cardiac death is the leading cause of death in the United States. Most sudden cardiac death is caused by ventricular fibrillation ("VF"), in which the heart's muscle fibers contract without coordination, thereby interrupting normal blood flow to the body. The only known effective treatment for VF is electrical defibrillation, in which an electrical pulse is applied to a patient's heart. The electrical shock clears the heart of the abnormal electrical activity (in a process called "defibrillation") by depolarizing a critical mass of myocardial cells to allow spontaneous organized myocardial depolarization to resume.

The electrical pulse must be delivered within a short time after onset of VF in order for the patient to have any reasonable chance of survival. To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero.

Importantly, the more time that passes, the longer the brain is deprived of oxygen and the more likely that brain damage will result. Electrical fibrillation may also be used to treat shockable ventricular tachycardia ("VT"). Accordingly, defibrillation is the appropriate therapy for any shockable rhythm, that is, VF or shockable VT.

One way of providing electrical defibrillation uses implantable defibrillators, which are surgically implanted in patients that have a high likelihood of experiencing VF. Implanted defibrillators typically monitor the patient's heart activity and automatically supply the requisite electrical defibrillation pulses to terminate VF. Implantable defibrillators are expensive, and are used in only a small fraction of the total population at risk for sudden cardiac death.

External defibrillators send electrical pulses to a patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators, collectively referred to as "AEDs", are becoming increasingly popular because relatively inexperienced personnel can use them. U.S. Pat. No. 5,607,454 to Cameron et al., entitled Electrotherapy Method and Apparatus, and PCT publication number WO 94/27674, entitled Defibrillator With Self-Test Features, the entire contents of the specifications of which are hereby incorporated by reference, describe AEDs.

AEDs provide a number of advantages, including the availability of external defibrillation at locations where external defibrillation is not regularly expected, and is likely to be performed quite infrequently, such as in residences, public buildings, businesses, personal vehicles, public transportation vehicles, among other locations. Although operators of AEDs can expect to use an AED only very occasionally, they must nevertheless perform quickly and accurately when called upon. For this reason, AEDs automate many of the steps associated with operating external defibrillation equipment. Along these lines, the operation of AEDs is intended to be simple and intuitive. AEDs typically are designed to minimize the number of operator decisions required.

SUMMARY OF THE INVENTION

The present invention provides a method for reducing delay between termination of cardiopulmonary resuscitation and administration of a defibrillating shock. According to the method, an electrocardiogram signal of the patient is monitored during administration of cardiopulmonary resuscitation to a patient. The electrocardiogram signal is analyzed to determine whether a shockable rhythm exists. It is indicated that a shockable rhythm exists and/or that a defibrillating shock will be administered. Cardiopulmonary resuscitation is stopped. The defibrillating shock is administered within 10 seconds of the cessation of cardiopulmonary resuscitation.

Additionally, the present invention provides a defibrillator. The defibrillator includes electrodes for monitoring a patient's heart rhythm during administration of cardiopulmonary resuscitation and producing an electrocardiogram signal corresponding to the patient's heart rhythm. A processor operatively connected to the electrodes receives the electrocardiogram signal from the electrodes and analyzes the patient's heart rhythm to detect a shockable rhythm. An indicator operatively connected to the processor indicates that a shockable rhythm exists and/or that a defibrillating shock is to be administered. Electrodes operatively connected to the power source administer a defibrillating shock to the patient within ten seconds of cessation of cardiopulmonary resuscitation.

Furthermore, the present invention concerns a method for reducing delay between termination of cardiopulmonary resuscitation and administration of a defibrillating shock. According to the method, an electrocardiogram signal of the patient is monitored during administration of cardiopulmonary resuscitation to a patient. The electrocardiogram signal is monitored to determine whether a shockable rhythm exists during administration of cardiopulmonary resuscitation to the patient. A defibrillator is automatically charged during the administering of the cardiopulmonary resuscitation.

Still further, the present invention provides a method for reducing delay between termination of cardiopulmonary resuscitation and administration of a defibrillating shock. The method includes administering the defibrillating shock within 10 seconds of cessation of cardiopulmonary resuscitation.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENTS

Figure 1:
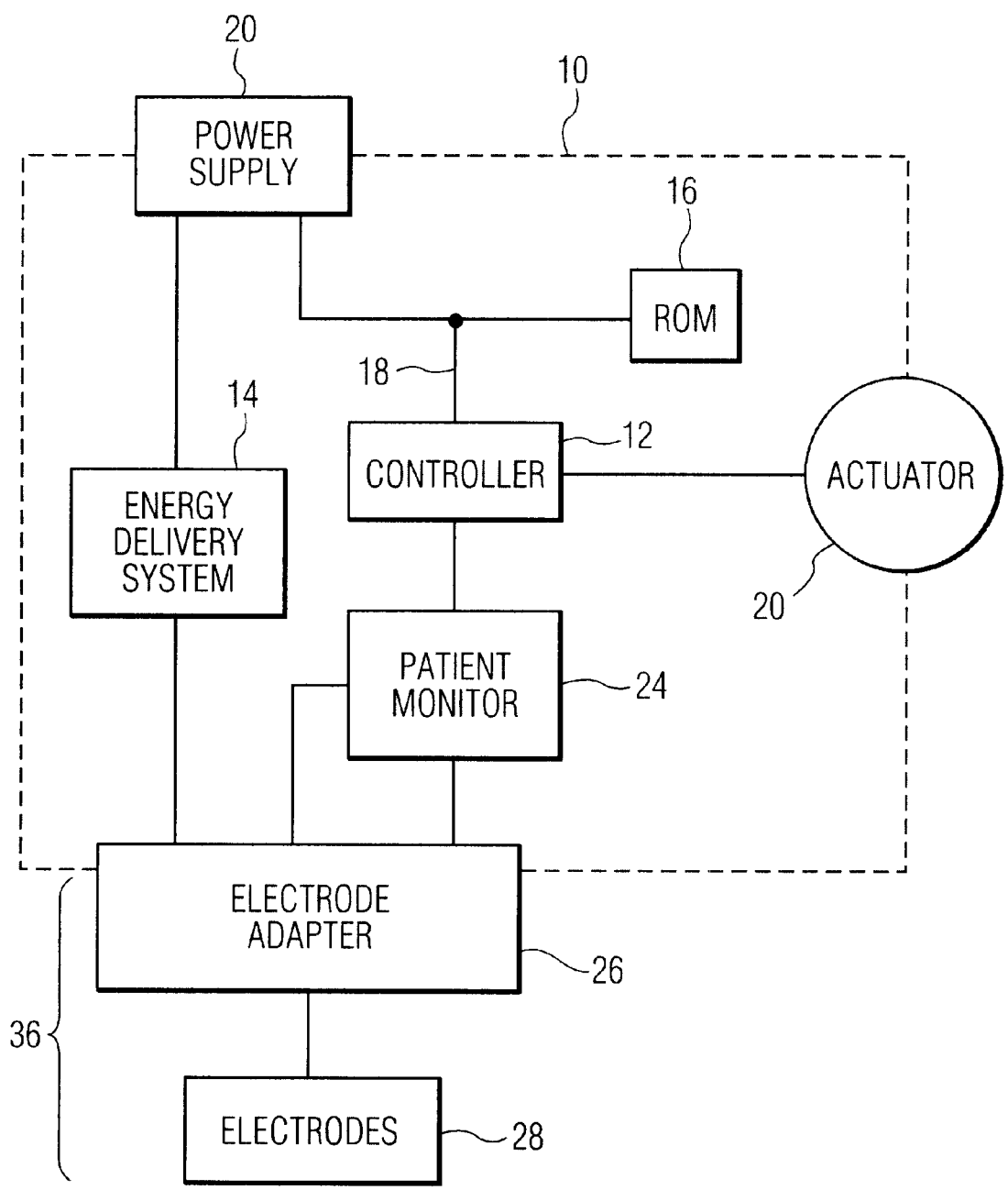
FIG. 1 represents a block diagram that illustrates elements of an electrotherapy device.

When utilizing a currently available AED, it is necessary to interrupt CPR on a patient while ECG analysis is performed in order to determine whether a shock is needed. If the patient requires a shock, CPR remains interrupted while the AED charges and then a shock is ultimately delivered. Total CPR interruption may be about thirty seconds or longer.

However, recent studies indicate that resuscitation success decreases markedly with CPR interruptions of the duration required by currently available AEDs. More recent work shows that continuing CPR until delivery of a defibrillating shock dramatically improves resuscitation success. Quite recently, work done at the direction of the assignee of the present invention indicates that the improved resuscitation success exists if CPR is interrupted for about 5 to about 10 seconds prior to delivery of the defibrillating shock.

The present invention addresses the need to permit rescuers to continue performing CPR until just prior to delivery of a defibrillating shock. The present invention can accomplish this in a number of ways. For example, the present invention can incorporate new signal processing in the form of new signal processing software and artifact rejection circuitry and associated electrodes to provide an accurate analysis of a patient's ECG signal and safe defibrillator charging with minimal or without any interruption of CPR on the patient.

The analysis may be carried out in a number of ways to permit a defibrillating shock to be administered within a short time after cessation of cardiopulmonary resuscitation. According to one embodiment, an adaptive filter is utilized in analyzing the ECG signal. Adaptive filters are discussed in greater detail in Adaptive Filter Theory, Third Edition, Prentice Hall, 1996, the entire contents of which are hereby incorporated by reference; chapters 7 and 9 are of particular relevance. In utilizing an adaptive filter, the present invention seeks to identify artifacts in the ECG signal that result from the occurrence of chest compressions during monitoring of the patient's heart rhythm. Employing the adaptive filter, the present invention then removes the artifacts to isolate the ECG signal and, thereby, more accurately determine whether a shockable rhythm exists. In effect, the present invention can "see through" the CPR artifacts to determine if a shockable rhythm exists.

According to one embodiment that utilizes an adaptive filter, the present invention analyzes an impedance channel. Such impedance channels are utilized in devices and methods for respiratory detection and measurement of cardiac output. By identifying changes in the impedance channel associated with the chest compressions carried out during CPR, the present invention can then determine where in the ECG signal disturbances related to the chest compressions are occurring and then isolate and eliminate the changes in the ECG signal. In such an embodiment, the impedance measurements may be carried out through existing electrodes for ECG monitoring and/or delivering a defibrillating shock.

With this or any embodiment of the present invention, the defibrillator may initiate charging of the defibrillator during monitoring of the patient's ECG and/or administration of CPR. Similarly, whether an adaptive filter is utilized or not, upon the detection of a shockable rhythm, the present invention can indicate at least that a shockable rhythm has been detected, that CPR should cease, and/or that physical contact with the patient should cease. If a shockable rhythm is detected, a defibrillating shock may then be delivered within about 10 seconds of the termination of CPR. After cessation of CPR and prior to delivering the shock, the present invention may quickly verify that a shockable rhythm exists. An impedance channel through the electrodes as discussed above may be utilized according to this embodiment. The impedance channel may be utilized during the period of time between cessation of CPR and delivery of the defibrillating shock to ensure that CPR is not restarted and/or to verify that a shockable rhythm exists. Typically, this embodiment includes performing an analysis to verify existence of a shockable rhythm during the period of time between cessation of CPR and delivery of the defibrillating shock.

According to another exemplary embodiment, the present invention analyzes the ECG similar to the second embodiment described directly above, but with out utilizing an impedance channel. Upon detection of a shockable rhythm, this embodiment assumes that CPR has ceased upon indication of the existence of a shockable rhythm, rather than utilizing an impedance channel to detect whether CPR restarts. The ECG signal will then be reanalyzed to verify that a shockable rhythm exists. The defibrillator will then administer a defibrillating shock or prompt a user to take action to initiate a defibrillating shock. If at any time after indicating that a shockable rhythm exists and before administering a defibrillating shock the defibrillator detects that CPR has been restarted, then the defibrillator will again execute a confirmatory reanalysis to verify that a shockable rhythm exists. It could be considered that such an embodiment is biased to proceed with delivery of a defibrillating shock, unless any event indicates otherwise.

Typically, the delay between interruption of CPR and administration of the defibrillating shock is less than about 10 seconds. A defibrillator according to the present invention includes a human interface that indicates to an operator when to perform certain actions, such as when to start and stop CPR, and when the defibrillator will perform certain actions, such as administering a defibrillating shock.

A defibrillator according to the present invention may be an automatic or a semiautomatic external defibrillator. An automatic defibrillator does not require any input from the operator to deliver a defibrillating shock. In general, a defibrillator according to the present invention includes monitoring electrodes for monitoring a patient's heart rhythm during administration of CPR and producing an ECG signal corresponding to the monitored rhythm.

The electrodes are operatively connected to a processor. The processor receives the signal supplied by the electrodes and analyzes the signal to determine whether the patient has a shockable rhythm.

External defibrillators for use by lay people with little or no training may include an interface for instructing an operator of the defibrillators. The interface can include an indicator for indicating when certain events are to occur. The interface can be operatively connected to the processor so that the processor can cause the indicator to produce indications at proper times.

An indicator according to the present invention can include one or more audible and/or visual indicators. For example, the indicators can include one or more light producing elements, such as light emitting diodes (LEDs), lights, or displays. One embodiment can include a display, such as a liquid crystal display or LED display that displays written instructions.

The indicator may alternatively or additionally include one or more audible display elements operatively connected to the processor. For example, the indicator may include a speaker that produces verbal commands informing the operator in care of a patient. Along these lines, the speaker could produce instructions on administration of CPR. Alternatively or additionally, the speaker could produce instructions for use of the defibrillator. Such instructions could include when to cease CPR and clear an area in the vicinity of a patient when a defibrillating shock is to be administered imminently as described herein. As described herein, according to the present invention, such an indication is produced within about 10 seconds prior to the administration of the defibrillating shock. Typically the indication is produced about 5 to about 10 seconds prior to the administration of the defibrillating shock.

In the case of an automatic defibrillator, the defibrillating shock would be delivered automatically, without any action by a user, such as pushing a button to deliver the shock. On the other hand, in the case of a semi-automatic defibrillator, the defibrillator would solicit an action by the user, such as pressing a button to deliver the defibrillating shock.

In addition to the above functions, an indicator according to the present invention may indicate when chest compressions are to be performed. For example, the indicator may act as a metronome, producing a tone or other audible signal each time that a chest compression is to be performed. The chest compression indicator may be separate from other indicator(s) that instruct an operator and indicate when a defibrillating shock is to be administered. A separate chest compression indicator could be operatively connected to the processor.

Regardless of how the chest compression indications are generated, the timing of the indications may be received by the processor wherein the processor accounts for the occurrence of chest compressions in the analysis of the patient's electrocardiogram signal, as discussed in greater detail above.

According to the present invention, monitoring of the heart rhythm takes place during the administration of CPR. In its analysis of the patient's heart rhythm, if the processor detects a shockable rhythm, the processor will automatically initiate charging of the defibrillator so that the defibrillator, also during administration of CPR. In contrast, currently available AEDs require cessation of CPR for monitoring to be carried out and for the operator of the defibrillator to initiating charging of the defibrillator if a shockable rhythm is detected. The present invention does not suffer from either of these disadvantages or the associated unfavorable implications to the patient.

Rather, monitoring electrodes will be placed on a patient upon the identification of a patient. Defibrillating electrodes may also be placed in contact with the patient at this time to be ready to deliver a defibrillating shock in the event a shockable rhythm is detected. CPR may then be commenced on the patient. Monitoring will take place during the administration of CPR. Once the processor determines that a shockable rhythm exists, the processor will initiate charge of the defibrillator, while CPR continues. Once the defibrillator is in a charged state, the indicator will indicate at least that a defibrillating shock will be administered to the patient imminently and that all people should clear an area in the vicinity of the patient for the shock to be administered.

Prior to the administering the defibrillating shock but after indicating that CPR should cease, the processor may again verify that a shockable rhythm exists. This verification is carried out in ten seconds or less between the termination of CPR and the delivery of the shock. However, unlike any analysis of the ECG during administration of CPR, analysis of the signal after cessation of CPR will deliver a "cleaner" signal, without any effects caused by the CPR and, hence, a more accurate analysis of the ECG signal. After delivery of the defibrillating shock, the indicator may indicate that CPR may again commence. A defibrillator may include separate indicators for indicating any one or more of the following that CPR should cease, the area in the vicinity of the patient should be cleared, a shock will be delivered imminently, and/or CPR should recommence.

After delivery of the defibrillating shock and/or after the restarting of CPR, the processor will again start to analyze the patient's heart rhythm to determine whether a shockable rhythm exists.

The following description provides description of a particular embodiment of an AED to facilitate understanding of the present invention. The AED described herein provides just one example of an AED that the system and method according to the present invention may be utilized with. FIG. 1 is a block diagram showing a device 10. Device 10 is an electrotherapy device. The device 10 may include the ability to defibrillate, cardiovert, or pace a patient, or a combination of these features. Device 10 has a controller 12 that operates an energy delivery system 14 and performs other aspects of the operation of the device. Software instructions for the operation of the device are accessible from read only memory (ROM), such as incorporated ROM 16. The controller accesses instructions for operation from ROM 16. It should be understood that, in this and other embodiments described below, "controller" means a microprocessor, controller, gate array, other control logic, or any combination of these elements.

Controller 12 communicates with ROM 16 via a memory bus 18. A recordable memory module 32 is attached to device 10 via an electrode system 36, as shown in FIG. 1. Electrode system 36 includes electrodes 28 and an electrode adapter 26.

Electrode adapter 26 is connected to electrodes 28 and is removably connected to the device 10. A suitable electrode system 36 adaptable for use in this invention would be, for example, Heartstream ForeRunner® electrodes.

Electrodes 28 communicate with a patient monitor 24 via electrode adapter 26 to provide patient ECG data from the patient to the patient monitor 24. Electrodes include electrodes capable of delivering defibrillation, monitoring a patient condition, delivering pacing pulses, or a combination of those features. In an AED, the patient monitor 24 monitors the patient for a heart rhythm and subsequently determines whether the monitored rhythm is shockable. When the rhythm is shockable, the patient monitor 24 then communicates a shock decision to the controller 12. The controller 12 then communicates to the energy delivery system 14. The energy delivery system 14 then delivers a therapeutic energy pulse to the patient (not shown) through electrodes 28 attached to the defibrillator 10 via electrode adapter 26, using the power supply 20 as the energy source.

The power supply may include elements such as batteries, a DC and/or an AC power source. The DC power source could be batteries. The power supply could also include a DC-DC and/or AC to DC converters. Additionally, the power supply could include a high voltage charge circuit. Furthermore, the power supply could include an energy storage capacitor.

Figure 2:
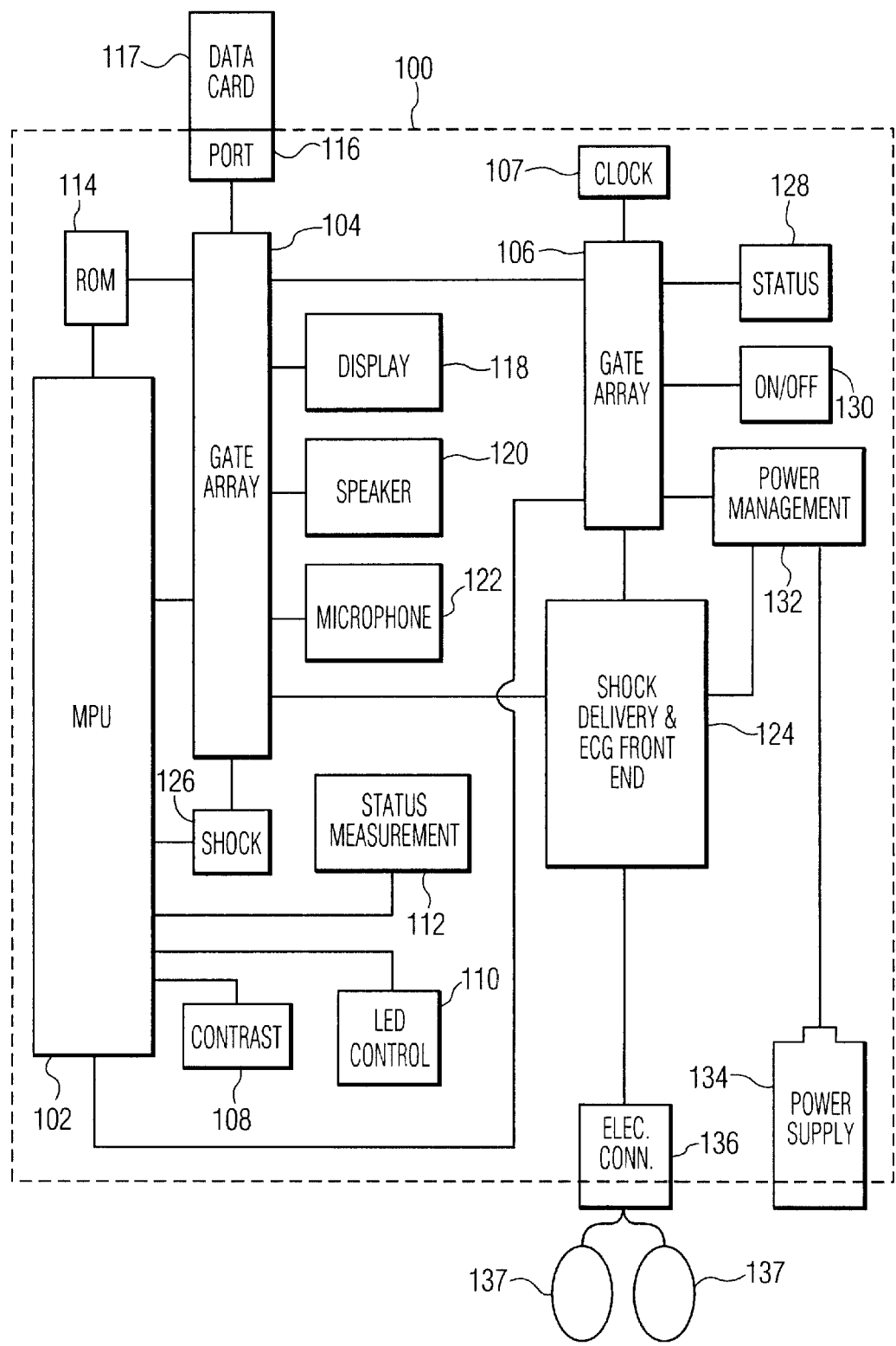
FIG. 2 represents a block diagram that illustrates major components of an automatic external defibrillator.

The major components of an AED are shown in FIG. 2 in block diagram form. Further detailed information about the operation of an AED can be obtained in U.S. Pat. No. 5,836,993, to Cole, for "Electrotherapy Device Control System and Method", and U.S. Pat. No. 5,593,427 to Gliner et al., for "Electrotherapy Method," the specifications of both of which are incorporated herein by reference. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat. No. 5,879,374, to Powers et al., for "External Defibrillator with Automated Self-Testing Prior to Use," the specification of which is incorporated herein by reference. Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No 5,735,879 to Gliner et al., for "Electrotherapy Method for External Defibrillators"; and U.S. Pat. No. 5,607,454, to Cameron et al. for "Electrotherapy Method and Apparatus"; the specifications of both of which are incorporated herein by reference.

The MPU can send and receive data and operational commands via the wireless communication port 138. This is used to assist manufacturing and to communicate status and use data to external devices. In addition, the port 138 permits remote operation of certain device features such as requesting and receiving device status.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. In addition, the operational characteristics of the defibrillator in any one of the modes can be changed as explained below.

Operation of the external defibrillator of this embodiment commences with the insertion of a power supply 134 or user activation of the power on button. Once gate array 106 confirms that a power supply 134 is inserted, gate array 104 prompts MPU 102 to begin its boot sequence. The boot sequence begins with MPU 102 sending out a series of addresses to ROM 114.

As is known in the art, while in patient treatment mode, the defibrillator 100 typically (1) determines whether electrodes 137 are attached to electrode connector 136; (2) receives ECG information from a patient through such electrodes; (3) analyzes the ECG information to determine whether a therapeutic shock is advised; and (4) delivers a shock to the patient through the electrodes 137 if a shock is advised and if the shock button 126 is actuated by a user.

A method according to the present invention includes monitoring an electrocardiogram signal of a patient during administration of CPR. The electrocardiogram signal is analyzed during administration of CPR to determine whether the patient has a shockable rhythm. During the administration of CPR, a defibrillator is charged if a shockable rhythm is detected. The defibrillator may be automatic or semi automatic. It is indicated at least to the person administering the CPR that a defibrillating shock is to be administered to the patient. The indication may be produced as described above and may include an indication to stop CPR and/or clear an area in the vicinity of the patient. The existence of a shockable rhythm may be verified at this point. A defibrillating shock is then delivered to the patient within about 10 seconds of the indication that the shock is to be delivered. The method may include indicating that CPR should recommence after delivery of the shock. After deliver of the defibrillating shock, the method may also include resuming monitoring of the patient's heart rhythm and analysis of the heart rhythm to determine whether a shockable rhythm still exists. In a semiautomatic defibrillator, the operator may initiate the delivery of the shock rather than having the shock automatically delivered. However, the monitoring, analysis, indicating and charging of the defibrillator may still occur as described above.

The method may also include periodically indicating when chest compressions should occur in the course of administering CPR. This indication may be tied in to the analysis of the patient's heart rhythm.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A method for reducing delay between termination of cardiopulmonary resuscitation and administration of a defibrillating shock, the method comprising:
    monitoring an electrocardiogram signal of the patient during administration of cardiopulmonary resuscitation to a patient;
    analyzing the electrocardiogram signal to determine whether a shockable rhythm exists;
    indicating at least one of that a shockable rhythm exists and that a defibrillating shock will be administered;
    ceasing cardiopulmonary resuscitation; and
    administering the defibrillating shock within 10 seconds of the cessation of cardiopulmonary resuscitation.

2. The method according to claim 1, further comprising:
    indicating that cardiopulmonary resuscitation should cease upon detecting a shockable rhythm.

3. The method according to claim 2, further comprising:
    indicating that a defibrillating shock will be administered when indicating that a shockable rhythm exists and that cardiopulmonary resuscitation should cease.

4. The method according to claim 1, further comprising:
    during the administering of the cardiopulmonary resuscitation automatically charging a defibrillator if the electrocardiogram signal indicates that the patient has a shockable rhythm.

5. The method according to claim 1, wherein the indication comprises at least one of audible indications and visual indication.

6. The method according to claim 1, wherein the indication comprises audible indications comprising spoken words.

7. The method according to claim 1, further comprising:
    periodically indicating when a chest compression should occur during the cardiopulmonary resuscitation.

8. The method according to claim 7, wherein the analysis of the electrocardiogram signal takes in to account occurrence of chest compressions.

9. The method according to claim 7, wherein the periodic indication comprises at least one of an audible and visual indication.

10. The method according to claim 1, further comprising:
    verifying that a shockable rhythm exists subsequent to termination of cardiopulmonary resuscitation and prior to administration of a shockable rhythm.

11. The method according to claim 1, further comprising:
    indicating that administration of cardiopulmonary resuscitation should be resumed subsequent to administration of the defibrillating shock.

12. The method according to claim 1, further comprising:
    indicating that administration of cardiopulmonary resuscitation should resume; and
    resuming monitoring an electrocardiogram signal of the patient and analyzing the electrocardiogram signal to determine whether a shockable rhythm exists subsequent to administration of a defibrillating shock.

13. The method according to claim 1, wherein the defibrillator is an automatic defibrillator.

14. The method according to claim 1, wherein the defibrillator is a semi-automatic defibrillator.

15. A method for reducing delay between termination of cardiopulmonary resuscitation and administration of a defibrillating shock, the method comprising:
    monitoring an electrocardiogram signal of the patient during administration of cardiopulmonary resuscitation to a patient;
    analyzing the electrocardiogram signal to determine whether a shockable rhythm exists during administration of cardiopulmonary resuscitation to the patient; and
    automatically charging a defibrillator during the administering of the cardiopulmonary resuscitation.

16. A defibrillator, comprising:
    electrodes for monitoring a patient's heart rhythm during administration of cardiopulmonary resuscitation and producing an electrocardiogram signal corresponding to the patient's heart rhythm;
    a processor operatively connected to the electrodes for receiving the electrocardiogram signal from the electrodes, analyzing the patient's heart rhythm to detect a shockable rhythm;
    an indicator operatively connected to the processor for indicating at least one of that a shockable rhythm exists and that a defibrillating shock is to be administered; and
    electrodes operatively connected to the power source for administering a defibrillating shock to the patient within ten seconds of cessation of cardiopulmonary resuscitation,
    wherein the indicator indicates that a defibrillating shock will be administered to the patient within ten seconds of the indication upon detection of a shockable rhythm.

17. The defibrillator according to claim 16, wherein the processor automatically initiates charging of the defibrillator upon detection of a shockable rhythm.

18. The defibrillator according to claim 16, wherein the electrodes for monitoring the patient's heart rhythm and administering a defibrillating shock to the patient are the same electrodes.

19. The defibrillator according to claim 16, wherein the defibrillator is an automatic external defibrillator.

20. The defibrillator according to claim 16, wherein the defibrillator is a semi-automatic external defibrillator.

21. The defibrillator according to claim 16, wherein the indicator produces at least one of audible and visual indication.

22. The defibrillator according to claim 16, wherein the indicator produces audible indications comprising spoken words.

23. The defibrillator according to claim 16, wherein the indicator indicates indicating when chest compressions should be administered to a patient.

24. The defibrillator according to claim 16, wherein the processor verifies that a shockable rhythm exists subsequent to termination of cardiopulmonary resuscitation and prior to administration of a shockable rhythm.

25. The defibrillator according to claim 16, wherein the indicator indicates that administration of cardiopulmonary resuscitation should cease and an area in the vicinity of the patient should be cleared prior to administration of the defibrillating shock and indicates that administration of cardiopulmonary resuscitation should be resumed subsequent to administration of the defibrillating shock.

26. The defibrillator according to claim 16, further comprising:
    a second indicator operatively connected to the processor for indicating that administration of cardiopulmonary resuscitation should cease and an area in the vicinity of the patient should be cleared prior to administration of the defibrillating shock and for indicating that administration of cardiopulmonary resuscitation should be resumed subsequent to administration of the defibrillating shock.

27. The defibrillator according to claim 16, herein the indicator indicates that administration of cardiopulmonary resuscitation should recommence, and wherein the processor resumes monitoring of the electrocardiogram signal of the patient and analyzing the electrocardiogram signal to determine whether a shockable rhythm exists subsequent to administration of a defibrillating shock.

28. The defibrillator according to claim 16, further comprising:
   a second indicator for indicating that administration of cardiopulmonary resuscitation should recommence, wherein the processor resumes monitoring an electrocardiogram signal of the patient and analyzing the electrocardiogram signal to determine whether a shockable rhythm exists subsequent to administration of a defibrillating shock.

29. A defibrillator, comprising:
   electrodes for monitoring a patient's heart rhythm during administration of cardiopulmonary resuscitation and producing an electrocardiogram signal corresponding to the patient's heart rhythm;
   a processor operatively connected to the electrodes for receiving the electrocardiogram signal from the electrodes, analyzing the patient's heart rhythm to detect a shockable rhythm;
   an indicator operatively connected to the processor for indicating at least one of that a shockable rhythm exists and that a defibrillating shock is to be administered;
   electrodes operatively connected to the power source for administering a defibrillating shock to the patient within ten seconds of cessation of cardiopulmonary resuscitation; and
   a chest compression indicator operatively connected to the processor for periodically indicating when chest compressions should be administered to a patient,
   wherein the analysis of the electrocardiogram signal takes in to account occurrence of chest compressions.

30. The defibrillator according to claim 29, wherein the periodic indication comprises at least one of an audible and visual indication.

* * * * *